(12) United States Patent
Park

(10) Patent No.: US 6,210,694 B1
(45) Date of Patent: Apr. 3, 2001

(54) COSMETIC COMPOSITION CONTAINING CHARCOAL AND PROCESS FOR THE PREPARATION THEREOF

(75) Inventor: Soon Ok Park, Seoul (KR)

(73) Assignee: Nesura Cosmetic Co., Ltd., Kyunggi-do (KR)

( * ) Notice: Subject to any disclaimer, the term of this patent is extended or adjusted under 35 U.S.C. 154(b) by 0 days.

(21) Appl. No.: 09/471,998

(22) Filed: Dec. 27, 1999

(30) Foreign Application Priority Data

Dec. 24, 1998 (KR) .................................... 98-58336
Dec. 22, 1999 (KR) .................................... 99-60094

(51) Int. Cl.⁷ ..................................................... A61K 7/48
(52) U.S. Cl. ............................................................. 424/401
(58) Field of Search ..................................... 424/401, 489, 424/195.1, 70.1; 514/844, 845, 846, 847, 848, 951, 952

(56) References Cited

U.S. PATENT DOCUMENTS

| | | | | |
|---|---|---|---|---|
| 4,037,543 | * | 7/1977 | Angelo ................................... | 110/14 |
| 5,310,568 | * | 5/1994 | Lini ...................................... | 426/422 |
| 5,439,858 | * | 8/1995 | Konishi .................................... | 502/7 |
| 5,785,977 | * | 7/1998 | Breithbarth ........................... | 424/401 |

* cited by examiner

*Primary Examiner*—Thurman K. Page
*Assistant Examiner*—Charesse L. Evans
(74) *Attorney, Agent, or Firm*—Birch, Stewart, Kolasch & Birch, LLP

(57) ABSTRACT

A cosmetic composition used in the treatment of skin which contains 5 to 20 parts by weight of charcoal based on 100 parts by weight of the cosmetic composition.

5 Claims, No Drawings

COSMETIC COMPOSITION CONTAINING CHARCOAL AND PROCESS FOR THE PREPARATION THEREOF

BACKGROUND OF THE INVENTION

1. Field of the Invention

The present invention relates to a cosmetic composition containing charcoal as a main ingredient and a method for its manufacture. More particularly, the present invention relates to an improved cosmetic composition containing charcoal which has an excellent adsorptive capacity for treating the skin and removing waste materials such as sebum, old corneous tissue or dust disposed on the skin.

2. Description of the Related Art

Various types of cosmetic compositions and methods for the preparation thereof are known in the art. Generally, the human skin is covered with skin oil, sweat, dust, old corneous tissue and cosmetic residue. Also, pimples develop on the human face in the summer months or at puberty and frequently sebhorreic dermatitis is produced from such pimples. Therefore, in order to clean the skin surface, a number of cosmetics have been developed. However, these conventional cosmetics do not provide the desired excellent improvement in the beauty treatment of the skin.

Even though charcoal has been utilized in cosmetic soaps, at the present time, such charcoal functions as a kind of abrasive cleanser. Therefore, charcoal has never been used in a cosmetic composition as a main ingredient for treating the skin in a beauty sense since the black coloration of the charcoal was thought to block an improvement in the beauty treatment of the skin. Thus, when conventional cosmetic soap containing charcoal is manufactured, there is the disadvantageous that the manufacturer must always keep in mind that the color of charcoal may adversely affect the skin.

SUMMARY OF THE INVENTION

Accordingly, it is an object of the present invention to provide an improved cosmetic composition containing charcoal as a main ingredient and a process for the preparation thereof which eliminates the above problems encountered with conventional cosmetic compositions and method for the preparation thereof.

Another object of the present invention is to provide a cosmetic composition containing charcoal as a main ingredient plus suitable amounts of a moisture agent, an additive agent, an oil, a preservative, an alcohol, a perfume and emulsifying agent for improving the beauty treatment of the skin and preventing the formation of black color on the skin.

A further object of the present invention is to provide a cosmetic composition containing charcoal for preparing various types of beauty treatments such as the peel-off type, the wash-off type, the sheet type pack and the cleansing cream and massage cream gel types so as to improve the removal of waste materials from the skin and provide an excellent non-harmful cosmetic effect for beautifying the skin.

Still another object of the present invention is to provide a method for the preparation of an excellent cosmetic composition from the charcoal as a main ingredient.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention is directed to a cosmetic composition containing charcoal which is present in an amount of 0.1 to 50 parts by weight, preferably 5 to 20 parts by weight, and having a particle size of about 200 to 500 mesh and to a process for the preparation thereof, for improving the beauty treatment of the skin which includes the removal of waste materials on the skin.

DESCRIPTION OF THE PREFERRED EMBODIMENTS

The present invention pertains to a cosmetic composition containing charcoal and a process for the preparation thereof. Particularly, the cosmetic composition of the present invention comprises 0.1–50 parts by weight of charcoal such as medicated charcoal, activated charcoal, etc. having a particle size of about 200 to 500 mesh improving the beauty treatment of the skin including the removal of waste materials such as skin oil, old corneous tissue or dust from the skin.

The charcoal having a particle size of 200 to 500 mesh includes charcoal having a plurality of pores having various types of pores for increasing the adsorptive capacity of the charcoal which, in turn, improves the adsorptive ability and moisture possessing ability of the cosmetic composition containing the charcoal. Also, medicated and activated charcoals are not harmful to the human body, and this provides an excellent cleansing effect for the skin.

The cosmetic composition containing charcoal can be used in various types of preparations, such as packs of a wash-off type, a peel-off type, and a sheet type, cleansing creams, massaging creams, and bath gels for preventing coloration from the charcoal on the skin.

The process for the preparation of the cosmetic composition containing charcoal as a main ingredient according to the present invention comprises dissolving and mixing about 50 to 99.9 parts by weight of suitable cosmetic agents at room temperature or an elevated temperature, and adding about 0.1 to 50 parts by weight of charcoal and emulsifying the mixture to prepare the various types of preparations as described in detail hereinafter. The charcoal is made from Korean pine tree, oak tree and bamboo and can be utilized as white charcoal and black charcoal and preferably medicinal charcoal and activated charcoal.

DETAILED DESCRIPTION OF THE INVENTION

The present invention will be described in more detail in connection with the following examples which should be considered as being exemplary and not limiting the present invention.

EXAMPLE 1

Wash-Off Type Pack

As shown in Table 1, 100 g of propylene glycol ($C_{11}H_{14}O_3$), 2 g of butylparahydroxybenzoate ($C_8H_8O_3$), (hereinafter quantum sufficient (q.s.) of fragrance are mixed all together and dissolved at a temperature of 65° C. to produce a first solution.

1 g of zanthan gum, 150 g of aluminum magnesium silicate, 2 g of dipotassium glycyrrhizinate ($C_{42}H_6K_2O_{16}$) is put into 534 g of purified water and dissolved at room temperature to produce a second solution. Thereafter, the first and second solutions are mixed to produce a mixed solution. 200 g of charcoal is added to the mixed solution for equivalently emulsifying the final product to provide a wash-off type product.

COMPARATIVE EXAMPLE 1

As shown in Table 1 a conventional product of Comparative Example 1 is produced by the same process and components of Example 1. The only difference is that an activated white clay or a mud is used in Comparative Example 1 instead of the charcoal of the Example 1.

COMPARATIVE EXAMPLE 2

As shown in Table 1, a conventional product of the Comparative Example 1 is produced by the same process and components with the exception that no activated white clay or mud is used as compared with Comparative Example 1.

TABLE 1

| No. | Name of Ingredient | Wash-Off Type Pack | Co. Ex. 1 Conven. | Co. Ex. 2 Conven. |
|---|---|---|---|---|
| | | (weight %) | | |
| 1 | purified water | 53.4 | 53.4 | 73.5 |
| 2 | xanthan gum | 1.0 | 1.0 | 1.0 |
| 3 | aluminum magnesium silicate | 15.0 | 15.0 | 15.0 |
| 4 | dipotassium glycyrrhizinate | 0.2 | 0.2 | 0.2 |
| 5 | propylene glycol | 10.0 | 10.0 | 10.0 |
| 6 | butyparahydroxy-benzoate | 0.2 | 0.2 | 0.1 |
| 7 | methylparahydroxy-benzoate | 0.2 | 0.2 | 0.2 |
| 8 | fragrance | q.s. | q.s. | q.s |
| 9 | charcoal | 20.0 | — | — |
| 10 | activated white clay | — | 20.0 | — | wherein q.s. is quantum sufficient.

EXPERIMENTAL EXAMPLE 1

(1) Test Method

Sixty females with ages of 15 to 40 years and defined by 20 dry skin females, 20 neutral skin females and 20 oily skin females were tested by applying the cosmetics of Example 1, Comparative Example 1 and comparative Example 2 as shown in Table 1 for 15 days.

(2) Evaluation Method

Based on an evaluation of the sebum adsorptive effect and the glossy skin effect, and using the following scale, below 20 is very bad;

below 20 to 40 is bade;

below 40 to 60 is normal;

below 60 to 80 is good; and 100 is very good.

The results are shown in Table 2.

(3) Resolution of Test

As shown in Table 2, the wash-off type pack (Example 1) according to the present invention had an excellent effect in sebum adsorptive effect and glossy skin effect when compared with conventional products (comparative Examples 1 and 2).

TABLE 2

| Item | Sebum Adsorptive Effect | Glossy skin Effect |
|---|---|---|
| <Dry skin female> | | |
| Example 1 | 86 | 86 |
| Comparative Example 1 | 78 | 80 |
| Comparative Example 2 | 60 | 56 |
| <Neutral skin female> | | |
| Example 1 | 90 | 90 |
| Comparative Example 1 | 82 | 80 |
| Comparative Example 2 | 56 | 50 |
| <Oily skin female> | | |
| Example 1 | 96 | 90 |
| Comparative Example 1 | 86 | 80 |
| Comparative Example 2 | 50 | 36 |

As shown in the above Table 2, in the oily skin female, the sebum adsorptive and glossy skin effect of the cosmetic composition according to the present invention shows an excellent effect.

EXAMPLE 2

Peel-Off Type Pack

As shown in Table 3 below, 10 g of allantoin ($C_4H_6N_4O_3$) and 30 g of propylene glycol ($C_3H_8O_2$) were put into 697 g of purified water and dissolved at a temperature of 80° C. Thereafter, 120 g of polyvinyl alcohol were added to the mixture for achieving a complete first solution. Also, into 50 g of SD alcohol ($C_6H_6O$), 2 g of methylparahydroxybenzoate ($C_8H_8O_3$) and q.s. of fragrance were added and dissolved at room temperature a second solution. The first and second solutions were mixed and 100 g of the charcoal of the present invention were added to the mixing solution for equivalently emulsifying the final product to provide a peel-off type pack.

COMPARATIVE EXAMPLE 3

As shown in Table 3, a conventional product of comparative Example 3 is produced by the same process and components except with no charcoal and compared with the Example 2.

TABLE 3

| No. | Name of Ingredient | Example 2 Peel-Off Type Pack | Com. Ex. 3 Conventional |
|---|---|---|---|
| | | (weight %) | |
| 1 | purified water | 69.7 | 79.7 |
| 2 | allantoin | 0.1 | 0.1 |
| 3 | propylene glycol | 3.0 | 3.0 |
| 4 | polyvinyl alcohol | 12.0 | 12.0 |
| 5 | SD alcohol | 5.0 | 5.0 |
| 6 | methylparahydroxy-benzoate | 0.2 | 0.2 |
| 7 | fragrance | q.s. | q.s. |
| 8 | charcoal | 10.0 | — |

EXPERIMENTAL EXAMPLE 2

(1) Test Method 60 females between the ages of 15 to 40 and defined as 20 dry skin females, 20 neutral skin females and 20 oily skin females were tested for 15 days by applying the cosmetics of Example 2, Comparative Example 3 as shown in Table 4.

(2) Evaluation Method

The evaluation method checked the sebum adsorption and old corneous tissue removing effects as shown in Table 4.

(3) Resolution of Test

As shown in Table 4, the peel-off type pack (Example 2) according to the present invention had an excellent effect in sebum adsorptive effect and old corneous tissue removing effect compared with the conventional product (Comparative Example 3).

TABLE 4

| Item | Sebum Adsorptive Effect | Old Corneous Tissue Removing Effect |
|---|---|---|
| <Dry skin female> | | |
| Example 1 | 90 | 96 |
| Comparative Example 3 | 56 | 70 |
| <Neutral skin female> | | |
| Example 1 | 92 | 90 |
| Comparative Example 3 | 54 | 56 |
| <Oily skin female> | | |
| Example 1 | 96 | 86 |
| Comparative Example 3 | 50 | 64 |

As shown in the above Table 4, the sebum adsorptive effect and the old corneous tissue removing effect of the cosmetic composition according to the present invention was very effective when treating oil skin females an the dry skin females.

EXAMPLE 3

Cleansing Cream

As shown in Table 5, 1 g of allantoin ($C_4H_6N_4O_3$), 30 g of potassium hydroxide (KOH) and 20 g of glycerin ($C_3H_8O_3$) were put into 346 g of purified water and heated to a temperature of 75° C. to produce a first solution.

Also, 30 g of stearic acid ($C_{18}H_{36}O_3$), 200 g of myristic acid ($C_{14}H_{28}O_2$), 20 g of lauric acid ($C_{12}H_{24}O_2$), 20 g of cetanol ($C_{16}H_{34}O$), 20 g of ethyleneglycol monostearate, 2 g of methylparahydroxybenzoate ($C_8H_8O_3$), 1 g of propylparahydroxybenzoate ($C_{10}H_{12}O_3$), and 30 g of coconut fatty acid diethanolamide were heated at a temperature of 75° C. to produce a second solution. Thereafter, the first and second solutions were mixed to produce a mixture solution and 100 g of charcoal and q.s. of fragrance were added to the mixture solution for equivalently emulsifying the final product so as to make a cleansing cream according to the present invention.

TABLE 5

| No. | Name of Ingredient | Example 3 Cleansing Cream | (weight %) Com. Ex. 4 Conventional |
|---|---|---|---|
| 1 | stearic acid | 3.0 | 3.0 |
| 2 | myristic acid | 20.0 | 20.0 |
| 3 | lauric acid | 2.0 | 2.0 |
| 4 | cetanol | 2.0 | 2.0 |
| 5 | ethylene glycol monostearate | 2.0 | 2.0 |
| 6 | methylparahydroxybenzoate | 0.2 | 0.2 |
| 7 | propylparahydroxybenzoate | 0.1 | 0.1 |
| 8 | coconut fatty acid diethanolamide | 3.0 | 3.0 |
| 9 | purified water | 34.6 | 44.6 |
| 10 | allantoin | 0.1 | 0.1 |
| 12 | glycerin | 20.0 | 20.0 |
| 13 | charcoal | 10.0 | — |
| 14 | fragrance | q.s. | q.s. |

EXPERIMENTAL EXAMPLE 3

(1) Test Method

This test method is the same as the Experimental Examples 1 and 2.

(2) Evaluation Method

As shown in Table 6, this evaluation method checked the cleansing and glossy skin effects. And at this time, the skin of the tested female was not classified.

(3) Resolution of Test

As shown in Table 6, the cleansing effect and the glossy skin effect were excellent.

TABLE 6

| Item | Cleansing Effect | Glossy Skin Effect |
|---|---|---|
| Example 3 | 96 | 94 |
| Comparative Example 4 | 78 | 64 |

EXAMPLE 4

Bath Gel

As shown in Table 7 below, 80 g of sodium lauryl sulfate ($C_{12}H_{25}NaO_4S$), 30 g of sodium polyoxyethylene laurylethyl sulfate, 30 g of triethanolamine lauryl sulfate ($C_{18}H_{41}NO_7S$), 1 g of citric acid ($C_6H_8O_7$), 2 g of imidazolidinyl urea ($C_{11}H_{16}N_8O_8$), and 0.5 g of disodium ethylenediaminetetraacetate ($C_{10}H_{16}N_2O_8 \cdot 2Na$) were dissolved in 706.5 g of purified water at a temperature of 70° C. to produce a first solution, and 30 g of glycerin ($C_3H_8O_3$), 10 g of ethyleneglycol monostearate, and 30 g of coconut fatty acid diethanolamide were dissolved at a temperature of 70° C. At this time, the above first and second solution were mixed to produce a mixture solution. 80 g of charcoal and q.s. fragrance were added to the mixture solution to make the bath gel according to the present invention.

COMPARATIVE EXAMPLE 5

As shown in Table 7 below, the conventional product (Comparative Example 5) is produced by the same process of the Example 4 except with no charcoal compared with Example 4.

TABLE 7

| No. | Name of Ingredient | Example 4 Bath Gel | (weight %) Com. Ex. 5 Conventional |
|---|---|---|---|
| 1 | purified water | 70.65 | 78.65 |
| 2 | sodium lauryl sulfate | 8.0 | 8.0 |
| 3 | sodium polyoxyethylene laurylethyl sulfate | 3.0 | 3.0 |
| 4 | triethanalamine lauryl sulfate | 3.0 | 3.0 |
| 5 | citric acid | 0.1 | 0.1 |
| 6 | imidazolidinyl urea | 0.2 | 0.2 |
| 7 | ethylenediaminetetra acetate | 0.05 | 0.05 |
| 8 | glycerin | 3.0 | 3.0 |
| 9 | ethyleneglycol monostearate | 1.0 | 1.0 |
| 10 | coconut fatty acid diethanolamide | 3.0 | 3.0 |
| 11 | charcoal | 8.0 | — |
| 12 | fragrance | q.s. | q.s. |

EXPERIMENTAL EXAMPLE 4

(1) Test Method

This test method is the same as the Experimental Example 1.

(2) Evaluation Method

As shown in Table 8, this evaluation checked the washing effect and glossy body effect. The evaluation method is the same as the Experimental Example 1.

(3) Resolution of Test

As shown in Table 8, the washing effect and the glossy body effect after bathing were excellent.

TABLE 8

| Item | Washing Effect | Glossy Body Effect After Bathing |
|---|---|---|
| Example 4 | 94 | 96 |
| Comparative Example 5 | 92 | 78 |

EXAMPLE 5

Massaging Cream

As shown in Table 9 below, 30 g of glycerin ($C_3H_8O_3$), 1 g of L-arginine ($C_6H_{14}N_4O_2$), 2 g of methylparahydroxybenzoate ($C_8H_8O_3$), 1 g of carboxyvinyl polymer were dissolved in 425 g of purified water and heated at a temperature of 80° C. to produce a first solution.

Also, 5 g of sorbitan monostearate ($C_{24}H_{46}O$), 10 g of PEG-40 stearate, 10 g of cetanol ($C_{16}H_{34}O$), 15 g of bees wax, 50 g of petrolatum, 400 g of mineral oil and 1 g of propylparahydroxybenzoate ($C_{10}H_{12}O_3$) were dissolved and heated at a temperature of 80° to produce a second solution. These first and second solutions were mixed to produce a mixture solution. 5 g of charcoal and fragrance were added to the mixture solution and emulsified equivalently to make a final product for use as a massaging cream.

COMPARATIVE EXAMPLE 6

As shown in Table 9, the conventional product of comparative Example 6 is produced by the same process and components as the process and components of Example 5, except with no charcoal.

TABLE 9

| No. | Name of Ingredient | Example 5 Massaging Cream | (weight %) Com. Ex. 6 Conventional |
|---|---|---|---|
| 1 | purified water | 42.5 | 47.5 |
| 2 | glycerin | 3.0 | 3.0 |
| 3 | L-arginine | 0.1 | 0.1 |
| 4 | methyparahydroxybenzate | 0.2 | 0.2 |
| 5 | carboxy vinyl polymer | 0.1 | 0.1 |
| 6 | sorbitan monostearate | 0.5 | 0.5 |
| 7 | PEG-40 stearate | 1.0 | 1.0 |
| 8 | cetanol | 1.0 | 1.0 |
| 9 | bees wax | 1.5 | 1.5 |
| 10 | petrolatum | 5.0 | 5.0 |
| 11 | mineral Oil | 40.0 | 40.0 |
| 12 | propylparahydroxybenzoate | 0.1 | 0.1 |
| 13 | charcoal | 5.0 | — |
| 14 | fragrance | q.s. | q.s. |

EXPERIMENTAL EXAMPLE 5

(1) Test Method

This test method is the same as the Experimental Examples 1, 2, 3 and 4.

(2) Evaluation Method

This evaluation method is the same as the Experimental Example 1.

(3) Resolution of Test

As shown in Table 10, the glossy body effect after massaging with the cosmetic composition of the present invention was excellent.

TABLE 10

| Item | Glossy Body Effect After Massaging With This Product |
|---|---|
| Example 5 | 95 |
| Comparative Example 6 | 76 |

EXAMPLE 6

Sheet-Type Pack

As shown in Table 11 below, 1 g of allantoin ($C_4H_6N_4O_3$), 20 g of propylene glycol ($C_3H_8O_2$), 1 g of glycerin ($C_3H_8O_3$) were dissolved in 477 g of purified water and heated at a temperature of 80° C. to produce a first solution.

100 g of polyvinyl alcohol, 50 g of polyvinyl pyrrolidone, and 200 g of polyacrylic acid were dissolved all together to produce a second solution.

20 g of SD alcohol, 2 g of methylparahydroxybenzoate ($C_8H_8O_3$) and q.s. of fragrance were added and dissolved to produce a third solution.

20 g of Kaolin and 10 g of charcoal were added to the mixture solution produced by mixing with the first, second and third solutions for producing a final product using a sheet-type pack according to the present invention.

COMPARATIVE EXAMPLE 7

As shown in Table 11, the conventional product of the Comparative Example 7 is produced by the process and components as Example 6 except with no charcoal.

TABLE 11

| No. | Name of Ingredient | Example 6 Sheet-Type Pack | (weight %) Com. Ex. 7 Conventional |
|---|---|---|---|
| 1 | purified water | 47.7 | 52.7 |
| 2 | allantoin | 0.1 | 0.1 |
| 3 | propylene glycol | 2.0 | 2.0 |
| 4 | glycerin | 1.0 | 1.0 |
| 5 | polyvinyl alcohol | 10.0 | 10.0 |
| 6 | polyvinyl pyrrolidone | 5.0 | 5.0 |
| 7 | polyacrylic acid | 20.0 | 20.0 |
| 8 | SD alcohol | 2.0 | 2.0 |
| 9 | methylparahydroxy-benzoate | 0.2 | 0.2 |
| 10 | fragrance | q.s. | q.s |
| 11 | Kaolin | 2.0 | 2.0 |
| 12 | charcoal | 5.0 | — |

EXPERIMENTAL EXAMPLE 6

(1) Test Method

This test method is the same as Experimental Example 1.

(2) Evaluation Method

As shown in Table 12, the evaluation checked the same as the Experimental Example 1 except with the classification of the application area of the human body.

(3) Resolution of Test

As shown in Table 12, the resolution of the test appeared to have an excellent effect.

TABLE 12

| Item | Adsorptive Effect |
|---|---|
| <Nose Area> | |
| Example 6 | 95 |
| Comparative Example 7 | 68 |
| <Chin Area> | |
| Example 6 | 91 |
| Comparative Example 7 | 63 |
| <Forehead> | |
| Example 6 | 90 |
| Comparative Example 7 | 61 |

Accordingly, the cosmetic composition containing charcoal and the process for the preparation thereof according to the present invention has various types of preparations such as packs of a wash-off type, a peel-off type, and a sheet type, cleansing creams, massaging creams and bath gels, so that it is easy for the consumer to select or choose a needed preparation depending on cosmetic needed time or usage. Also, since the charcoal possesses pore capacity, moisture possessing ability, adsorptive capacity and preservative ability, the cosmetic composition of the present invention has an excellent cosmetic effect for the human body.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A cosmetic composition used in the treatment of skin, said composition containing 5 to 20 parts by weight of charcoal based on 100 parts by weight of the cosmetic composition, said charcoal being obtained from the Korean pine tree, the oak tree and the bamboo tree.

2. The cosmetic composition of claim 1, wherein the charcoal has a particle size of about 200 to 500 mesh.

3. The cosmetic composition of claim 1, wherein the cosmetic composition is a peel-off composition, a wash-off composition, a sheet pack composition, a cleansing cream composition and a massage cream gel composition.

4. The cosmetic composition of claim 1, wherein the charcoal is medicated charcoal and activated charcoal.

5. A method of treating oily skin, neutral skin and dry skin which comprises applying a cosmetic composition to the skin, said composition containing charcoal which is present in an amount of 5 to 20 parts by weight based on 100 parts by weight of the cosmetic composition, said charcoal being obtained from the Korean pine tree, the oak tree and the bamboo tree.

* * * * *